United States Patent
Burlingame et al.

(10) Patent No.: US 7,138,228 B2
(45) Date of Patent: Nov. 21, 2006

(54) PROTEIN O-SULFONATION

(75) Inventors: Alma L. Burlingame, Sausalito, CA (US); Katalin F. Medzihradszky, San Francisco, CA (US); Zsuzsanna Darula, Boulder, CO (US); Eran Perlson, Givat Shmuel (IL); Michael Fainzilber, Rehovot (IL); Robert J. Chalkley, San Francisco, CA (US); Darren Tyson, Aliso Viejo, CA (US); Ralph A. Bradshaw, Lake Forest, CA (US)

(73) Assignees: Regents of the University of California, Oakland, CA (US); Yeda Research and Development Co. Ltd. at the Weizmann Institute of Science, Oakland, CA (US)

( * ) Notice: Subject to any disclaimer, the term of this patent is extended or adjusted under 35 U.S.C. 154(b) by 445 days.

(21) Appl. No.: 10/657,027

(22) Filed: Sep. 5, 2003

(65) Prior Publication Data
US 2005/0054020 A1    Mar. 10, 2005

(51) Int. Cl.
*C12Q 1/00*    (2006.01)
*C12Q 1/48*    (2006.01)
*C12Q 1/44*    (2006.01)
*C12P 21/04*   (2006.01)
*G01N 33/53*   (2006.01)

(52) U.S. Cl. .............................. 435/4; 435/15; 435/19; 435/70.21; 435/7.1

(58) Field of Classification Search ............... 435/69.1, 435/252
See application file for complete search history.

(56) References Cited

OTHER PUBLICATIONS

Hiltz et al. PNAS 1955, 41, 880.*
Bettelheim et al. JACS 1954, 76, 2838-2839.*
Conboy et al. J. Am.SOc Mass Spect 1992, 3, 804-814.*

* cited by examiner

Primary Examiner—Rebecca E. Prouty
Assistant Examiner—Mohammad Meah
(74) Attorney, Agent, or Firm—Richard Aron Osman

(57) ABSTRACT

Post-translational O-sulfonation of a serine or threonine residue of proteins is detected, optionally comparatively, wherein the detected O-sulfonation is detected under a first physiological condition, and is compared with a control O-sulfonation detected under a second physiological condition, and a difference between the detected and control O-sulfonations indicates a difference between the first and second physiological conditions. Predetermined changes in physiological conditions are used to infer specific changes in O-sulfonation. Proteins are modified by introducing a predetermined change in O-sulfonation at a serine or threonine residue of the protein, and optionally, detecting a resultant change in O-sulfonation. These methods include introducing or increasing O-sulfonation, eliminating or reducing O-sulfonation; and derivatizing or substituting O-sulfonation.

6 Claims, No Drawings

PROTEIN O-SULFONATION

This work was supported by NIH NCRR Grant, RR 01614. The U.S. government may have rights in any patent issuing on this application.

INTRODUCTION

1. Field of the Invention

The field of the invention is detecting and modulating O-sulfonation of serine and threonine residues on polypeptides.

2. Background of the Invention

Sulfonation occurs as a common enzymatic modification of endogenous substances including proteins, carbohydrates, catecholamines, and estrogenic steroids as well as xenobiotic chemicals [1]. Sulfonation refers to the transfer of the sulfonate group ($SO_3^{-1}$) from 3'-phosphoadenosine-5'-phosphosulfate (PAPS), the only known sulfonate donor [2]. Sulfonation can occur through several types of linkages, esters (O-sulfonation), amides (N-sulfonation) and thioesters (S-sulfonation) [3], of which O-sulfonation is the most prominent. The transfer of $SO_3^{-1}$ to a hydroxyl acceptor (O-sulfonation) generates an ester sulfate, and this reaction has commonly been referred to as sulfation rather than the more accurate O-sulfonation.

The majority of cellular sulfonation is O-sulfonation and occurs primarily on steroids, catecholamines and thyroid hormones [1]. The sulfonation of these molecules is catalyzed by the soluble cytosolic sulfotransferases and appears to alter their bioactivity. For example, estrogen, testosterone and thyroid hormones ($T_3$ and $T_4$) can interact with their respective receptors to regulate transcription whereas their sulfate-containing moieties cannot. Furthermore, the half-life of these compounds in blood is significantly shorter than that of their conjugated counterparts suggesting that sulfonation maintains these compounds in an inactive state ready for rapid deployment by the removal of the sulfonyl group.

While the cytosolic sulfotransferases conjugate cell-permeable or intracellular compounds, the membrane-bound Golgi-associated sulfotransferases are primarily responsible for sulfonation of extracellular proteins via a co- or post-translational mechanism. The membrane-bound sulfotransferases are responsible for the sulfonation of various glycosaminoglycans such as heparin and heparan sulfate. Additionally, such enzymes catalyze the direct sulfonation of proteins on the 4-O-position of tyrosine residues [4]. It is one of the last modifications to occur during protein transiting the trans-Golgi and thus has been found almost exclusively on secreted and plasma membrane proteins of all metazoan species examined. In addition, there is a large body of evidence that this modification is present usually at the interface of interacting proteins and hence, is known to modulate extracellular protein-protein interactions. In humans, protein tyrosine sulfonation has been implicated in proteins of the vasculature and hemostasis. Examples include the mediation of inflammatory leukocyte adhesion, chemokine receptors and modulation of the blood coagulation cascade [5]. Significantly, only tyrosine residues have been described as sites for O-sulfonation within proteins, and O-sulfonation of proteins has not previously been shown to occur within the cytosol. Several tyrosyl protein sulfotransferases [6,7] and arylsulfatases [8] present in the trans-Golgi have been described, but unlike tyrosine phosphorylation/dephosphorylation [9], there is no evidence of dynamic regulation of tyrosine sulfonation [4,5]. Until now, only widespread modification of tyrosine has been observed [10,11].

We have discovered the occurrence of sulfonation as a posttranslational modification of serine and threonine residues, and that this sulfonation is involved in the modulation of protein-protein interactions, and in particular, has regulatory functions in receptor tyrosine kinase signaling as discussed further below. We have exploited this finding to develop methods of detecting and modulating this serine and threonine sulfonation.

SUMMARY OF THE INVENTION

The invention provides methods and compositions for detecting and/or modulating O-sulfonation of serine or threonine residues on cell-made polypeptides. In one embodiment, the invention provides a method of detecting a post-translational protein modification, comprising the step of: specifically detecting O-sulfonation of a serine or threonine residue of the protein. This method may be practiced comparatively, wherein the detected O-sulfonation is detected under a first physiological condition, and is compared with a control O-sulfonation detected under a second physiological condition, particularly wherein a difference between the detected and control O-sulfonations indicates a difference between the first and second physiological conditions. The detected and control O-sulfonations may be detected directly, indirectly (e.g. by specifically detecting a biochemical marker predetermined to be specifically correlated with the change in O-sulfonation) or inferentially (e.g. by specifically detecting a physiological change predetermined to be specifically correlated with the change in O-sulfonation).

Also disclosed are diagnostic reagents specific for O-sulfonated proteins, particularly antibodies which specifically bind incorporated O-sulfonated serine or threonine residues. Accordingly, the invention provides an isolated antibody which specifically binds an O-sulfonated protein, wherein the specific binding is dependent on the presence of an O-sulfonated serine or threonine residue in the protein.

In another embodiment, specific, predetermined changes in physiological conditions (including biochemical signaling) are used to infer specific changes in O-sulfonation. For example, this embodiment includes a method of detecting a change in O-sulfonation of a serine or threonine residue of a protein, comprising the step of specifically detecting a physiological change predetermined to be correlated with the change in O-sulfonation.

In another embodiment, the invention provides a method of detecting a serine or threonine protein sulfotransferase or sulfatase activity, comprising the step of: specifically detecting a change in O-sulfonation of a serine or threonine residue of a protein, wherein the change in O-sulfonation indicates the sulfotransferase or sulfatase activity.

In another embodiment, the invention provides methods of modifying proteins by introducing a predetermined change in O-sulfonation at a serine or threonine residue of the protein, and optionally, detecting a resultant change in O-sulfonation, for example, by specifically detecting a physiological change predetermined to be correlated with the change in O-sulfonation. These methods include introducing or increasing O-sulfonation at the serine or threonine of the protein; eliminating or reducing O-sulfonation at the serine or threonine of the protein; and derivatizing or substituting O-sulfonation at the serine or threonine of the protein.

In another embodiment, the invention provides kits comprising a reagent for use in a subject method, and optionally, an instructional medium describing a subject method. The invention also provides business methods specifically adapted to, and/or incorporating a description of, or reference to a subject method or kit.

DETAILED DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or.

Protein sulfonation on serine and threonine residues is a natural post-translational modification of numerous and diverse proteins, particularly in eukaryotic organisms. Serine and threonine sulfonation is used to regulate a broad and diverse array of protein functions, including assembly and signal transduction. This invention provides methods and compositions for detecting and/or modulating natural and artificial O-sulfonation of serine or threonine residues on proteins. The methods are applicable to an enormous diversity of natural and non-natural proteins, including intracellular, membrane-bound, and extracellular proteins, wherein the term protein generically encompasses biomolecules comprising a peptide-bond linked amino acid polymer (i.e. peptide or polypeptide) made by a cell, and includes such polymers subject to post-translation modifications, including glycosylation, and joined to other biomolecules (e.g. to form proteo-lipids), or incorporated into larger macromolecules. Preferred target proteins are human proteins, particularly human blood proteins.

Described below are diverse exemplary methods of using and commercially exploiting O-sulfonation of the serine or threonine residue of the protein. Of course, the invention includes existent methods and uses relating to tyrosine sulfonation and phosphorylation and glycosylation of serine and threonine residues, as adapted to sulfonated serine and threonine residues; e.g. Bettelheim, J Am Chem Soc., 1954, 76, 2838–2839; Hiltz et al. PNAS 1955, 41, 880; Leyh, Revs Biochem and Mol. Biol., 1993, 28, 515–542.

O-sulfonation of the serine or threonine residue of the protein may be specifically detected by any convenient analytical technique, including specific chemical reagents, such as antibodies specific to the modified residues, chemical analysis, which may be performed directly or by derivatizing the O-sulfonated groups and detecting the resultant product, radiolabeling, such as with $^{35}SO_4$, and mass fragmentation analysis by mass spectrometry.

For sensitive detection, high performance hybrid triple quadrupole/linear ion trap mass spectrometers are particularly amenable. For example, the recent ABI/Sciex QTRAP4000 (Applied Biosystems, Foster City, Calif.) detects and selectively sequences phospho-versus sulfo peptides via observation of m/z=−79 vs −80 during a HPLC run of a protein digest. Another instrument, the Thermo Finnigan (San Jose, Calif.) LTQ FT-ICR ESI System is able to measure masses accurately within 1 ppm—revealing differences in accurate mass between HP-(30.97376+1.007825) and S-(31.97207) nominal mass isobars. Equipped with electron capture dissociation (ECD) that selectively cleaves peptide backbone bonds and leaves weaker, chemically labile posttranslational bonds intact, this system accelerates the site specific localization of phospho versus sulfo Ser/Thr and O-GlcNAc.

Detection reagents comprising O-sulfonated serine and threonine-specific moieties include somatically recombined polypeptide receptors like specific antibodies or T-cell antigen receptors (see, e.g Harlow and Lane (1999) Using Antibodies, A Laboratory Manual, Cold Spring Harbor Laboratory Press), intracellular binding agents identified with assays such as one-, two- and three-hybrid screens, non-natural intracellular binding agents identified in binding assays of chemical libraries, etc. In particular, protocols for generating specific monoclonal and polyclonal antibodies are well-known, including human, humanized, and hybrid human-murine antibodies. In general, sulfopeptide-specific antibodies may be made by covalently coupling the sulfopeptide to a complex antigen, and emulsifying the conjugate in an adjuvant, such as Freunds complete adjuvant. Laboratory animals, such as rabbits are immunized according to conventional protocol and bled. Alternatively, protocols for in vitro immunization are also well known. The presence of specific antibodies may be assayed by convenient solid phase immunosorbant assays using immobilized sulfo-peptides, and to ensure specificity, the corresponding negative control non-sulfonated peptide. Positive and negative affinity purification is readily effected using immobilized sulfo-peptides and negative control peptides.

Protocols for generating antibodies to poorly immunogenic epitopes are well known in the art; e.g. the use of antigen-selected combinatorial phage antibody libraries (e.g. Williamson et al. 1998, J Virol 72, 9413–18). In particular protocols designed to maximize yield of sulfopeptide-specific antibodies, we conjugate sulfopeptides having lengths between 5 and 15 residues, at >90–96% purity, immunize at least 3 animals, and affinity purify the antibodies over both the non-sulfopeptide and sulfopeptide-Sepharose. Using these criteria, we describe how to generate a panel of O-linked serine- and threonine-sulfonated peptide specific monoclonal antibodies using a panel of corresponding O-linked serine- and threonine-sulfonated peptides conjugated to keyhole limpet hemocyanine (KLH); see Examples, below. Hence, also disclosed are diagnostic antibody reagents which specifically bind incorporated O-sulfonated serine or threonine residues. Accordingly, the invention provides an isolated antibody which binds specifically an O-sulfonated protein, wherein the specific binding is dependent on the presence of an O-sulfonated serine or threonine residue in the protein. These specific binding agents may be modified or derivatized, for example with a label, to provide convenient reporters.

The methods encompass detecting a plurality of different and often predetermined, different serine and threonine sulfonations, which may be on one or more proteins. Specific sulfonation patterns are associated with particular proteins, and particular conditions. Hence, serine and threonine sulfonation, and patterns thereof, are used to characterize proteins and physiological conditions, and vice versa. In particular, specific, predetermined changes in physiological conditions (including biochemical signaling) are used to infer specific changes in O-sulfonation. For example, this embodiment includes a method of detecting a change in O-sulfonation of a serine or threonine residue of a protein, comprising the step of specifically detecting a physiological change predetermined to be correlated with the change in O-sulfonation.

Detection methods may be practiced comparatively, wherein the detected O-sulfonation is detected under a first physiological condition, and is compared with a control O-sulfonation detected under a second physiological condition, and a difference between the detected and control O-sulfonations indicates a difference between the first and second physiological conditions. Hence, a physiological change, preferably predetermined, is detected inferentially by detecting a change in O-sulfonation of a serine or threonine residue of a protein, also preferably predetermined, wherein the change in O-sulfonation of the serine or threonine residue of the protein indicates the physiological change. Analogously, the invention provides methods for detecting a change in O-sulfonation of a serine or threonine residue of a protein by detecting a physiological change predetermined to be correlated with the change in O-sulfonation.

In natural cells, numerous serine and threonine protein sulfotransferases and sulfatases effect serine and threonine O-sulfonation and desulfonation. Additionally, O-sulfonated serine and threonine residues mediate their functionalities by participating in a wide variety of intermolecular interactions with natural, specific interacting molecules, particularly proteins. These natural interacting molecules, particularly proteins, and particularly sulfotransferases and sulfatases, are readily detected and isolated using O-sulfonated serine- and threonine containing peptides and proteins in established affinity strategies, including affinity chromatography, two-hybrid screening, affinity panning, etc. These sulfotransferases and sulfatases may also be detected by specifically detecting a change in O-sulfonation of a serine or threonine residue of a protein, particularly a predetermined change predetermined to be correlated with a predetermined sulfotransferase or sulfatase, wherein the change in O-sulfonation indicates the sulfotransferase or sulfatase activity.

Natural, specific interacting molecules, and derivatives, including deletion mutants thereof which retain binding specificity, provide specific probes for detecting incorporated O-sulfonated serine or threonine residues. Hence, also disclosed are diagnostic reagents specific for O-sulfonated proteins, in addition to antibodies, which specifically bind incorporated O-sulfonated serine or threonine residues. As with specific antibodies, these specific binding agents may be modified or derivatized, for example with a label, to provide convenient reporters.

In another embodiment, the invention provides methods of modifying proteins by introducing a preferably predetermined change in O-sulfonation at a serine or threonine residue of a preferably predetermined protein, and optionally, detecting a resultant change in O-sulfonation, for example, by specifically detecting a physiological change predetermined to be correlated with the change in O-sulfonation. The modification may be made inside or outside the cell expressing the protein. These methods include introducing or increasing O-sulfonation at the serine or threonine of the protein; eliminating or reducing O-sulfonation at the serine or threonine of the protein; and derivatizing or substituting O-sulfonation at the serine or threonine of the protein. Generally, the methods are practiced by directly or indirectly activating or inhibiting a preferably specific serine/threonine sulfatase or sulfotransferase. For example, eliminating or reducing O-sulfonation at the serine or threonine of the protein may be effected with a serine/threonine sulfotransferase inhibitor (e.g. Armstrong, et al. Curr. Opin. Drug Disc. Dev., 2000, 3, 502–515), such as a carbohydrate sulfotransferase inhibitor (e.g. Armstrong et al., Chem. Int. Ed. Engl. 39, 1303–1306, 2000), a purine sulfotransferase inhibitor (e.g. Verdugo, et al. J. Med. Chem., 2001, 44, 2683–2686), a bisubstrate sulfotransferase inhibitor (e.g. Armstrong, et al. Org. Lett. 2001, 3, 2657–2660; Armstrong et al. J Org Chem. 2003, 68, 170–3) and combinatorial target-guided ligand assembly generated sulfotransferase inhibitors (e.g. Kehoe et al., Bioorg Med Chem Lett. 2002, 12, 329–332).

In this regard, we disclose cross-talk between several post-translational serine/threonine O-linked modifications, including O-linked glycosylation (e.g. GlcNAc), O-linked sulfonation, and O-linked phosphorylation. Since these alternative modifications can occupy the same serines and threonines, they can be interdependently regulated. For example, selective inhibition of O-linked glycosylation and phosphorylation can be used to promote O-linked sulfonation at the same site. Methods and reagents for regulating O-linked phosphatases and kinases are well known in the art, as are analogous methods for regulating O-linked carbohydrate transferases and sulfatases (e.g. Winans et al. Chem Biol. 2002, 9, 113–129; Grunwell et al. Biochem. 2002, 41, 13117–13126) and O-linked phosphotransferases.

Methods for inducing beta elimination and Michael addition to O-GlcNAc sites are well-established (Vosseler et al., 2002, Curr Opn Chem Biol 6, 851–7), and analogous protocols are established for modifying phosphorylation sites (e.g. Knight et al., Nat Biotechnol. 2003 Aug. 17, Epub ahead of print). Hence, O-GlcNAc modifications on serine and threonine, and serine-phosphate may be beta eliminated, and then modified by any selected Michael reagent. Selectivity of the modification may be enhanced, for example, by treating a target protein with a phosphatase to remove phosphorylation-sites and then beta-eliminating to get O-GlcNAC sites, etc. O-sulfo-serine and -threoine sites can be similarly beta-eliminated and labeled.

For example, Wells, et al. (2002, Mol Cell Proteomics 1(10), 791–804) describe beta-elimination/Michael addition method protocols for mapping sites of O-modification using affinity tags for serine and threonine post-translational modifications, including modifications that rely on mild beta-elimination followed by Michael addition with reagents such as dithiothreitol. The reference also recites methods for using synthetic peptides wherein biotin pentylamine replaces dithiothreitol as the nucleophile. The modified peptides can be efficiently enriched by affinity chromatography, and the sites can be mapped using tandem mass spectrometry. This same methodology can be applied to mapping sites of serine and threonine sulfonation, and provides a strategy that uses modification-specific antibodies and enzymes to discriminate between sulfonation, phosphorylation and GlcNAC O-serine and O-threonine post-translational modifications.

Proteins and peptides containing or modified to contain predetermined O-serine or O-threonine sulfonation provide a wide variety of industrial uses, including immunogens for eliciting specific antibodies, antigens for detecting such antibodies or for use in affinity binding pairs with such antibodies, labels or affinity reagents for binding sulfatases and sulfotransferases, competitive inhibitors of sulfo-protein specific interaction etc. For example, O-serine sulfonated peptides can be shown to inhibit native sulfonation-dependent protein-protein interactions using methods analogous to those of Roos et al. 1997, Mol Cell Biol, 17, 6472–80.

The invention also provides kits specifically tailored to practicing the subject methods. For example, in one embodiment, the kits comprise one or more materials for detecting or modifying a preferably predetermined O-sulfonation of serine or threonine of a preferably predetermined protein and an associated instructional medium describing a subject method.

The invention also provides business methods specifically tailored to practicing the subject methods. For example, in one embodiment, the business methods comprise selling, contracting, or licensing a subject method or composition for detecting or modifying a preferably predetermined O-sulfonation of serine or threonine of a preferably predetermined protein.

EXAMPLES

I. Identification and Isolation of Differentially Serine and Threonine O-Sulfonated Proteins.

Here we report the discovery and structural characterization of O-sulfonation of both serine and threonine residues in proteins of diverse class and function isolated from eukaryotes spanning the range from a unicellular parasite to humans. These include a neuronal intermediate filament protein from the snail (*Lymnaea stagnalis*), a cathepsin—C like protein from the protazoan malaria parasite (*Plasmodium falciparum*) and cytoplasmic constructs of the human orphan receptor tyrosine kinase, Ror2. The presence of this new posttranslational protein modification was detected and characterized by on-line HPLC-tandem electrospray mass spectrometry from proteins isolated by SDS-PAGE.

Proteins isolated from *Lymnaea stagnalis* nerve axoplasm were subjected to 2D-gel screening. Differentially expressed protein spots were visualized by a mass spectrometric compatible silver stain, excised, digested in-gel with trypsin, and analyzed by LC-CIDMS (see below). Tryptic peptide sequences were deduced from interpretation of the collision-induced dissociation (CID) spectra measured [12]. Our Bogyo malaria protein isolation protocol has been previously described [14].

The transmembrane and cytoplasmic domains of human Ror2 were amplified by RT-PCR from total RNA isolated from human SH-SY5Y cells. The cDNA, encompassing residues 427–943 with an XhoI site in place of the stop codon, was subcloned into pcDNA6-Myc/His-A (Invitrogen) to add a carboxyl-terminal Myc/His tag resulting in the plasmid termed pc6-Ror2cytoMH. To target the Ror2 construct to the inner surface of the membrane, the chicken c-Src myristylation signal was added to the amino terminus starting at residue 432 using the unique SgrAI site within the myristylation sequence, creating the pc6-myrRor2cytoMH vector. Residues 749–943 were deleted from the construct by generating a PCR fragment with an XhoI site after residue 748 to create the pc6-myrRor2DMH vector.

Human embryonic kidney 293T cells were cultured in Dulbecco's Modified Eagle's Medium containing 10% fetal bovine serum and 1% penicillin/streptomycin solution (Invitrogen). Approximately 800,000 cells were seeded per 60 mm dish and transiently transfected using LipofectAMINE™ 2000 (Invitrogen) according to the manufacturer's recommended protocol. Cells were incubated for 48 hours prior to harvesting. Cells were washed twice with ice-cold phosphate-buffered saline and scraped into 750 mL of the same solution. Cells were pelleted by centrifugation at ~5,000×g for 1 min and supernatant was removed by aspiration. Cells were lysed in a protein extraction buffer (PEB) and cleared by centrifugation at ~14,000×g for 10 min at 4° C. Myc/His tagged proteins were immunoprecipitated by incubating 1 mg of each sample with 15 mL of agarose-conjugated anti-myc antibody overnight at 4° C. Agarose beads were washed twice with PEB and once in a kinase buffer. Beads were then incubated in kinase buffer containing 100 mM ATP for 30 min at 30° C. Reactions were stopped by the addition of 5 mL 6×SDS-PAGE loading buffer.

The digests and synthetic peptides were analyzed by capillary HPLC-ESI-QqoaTOFMS using an Ultimate HPLC system equipped with a FAMOS autosampler and a C18 PepMap 75 mm×150 mm column (Dionex-LC-Packings, San Francisco). Solvent A was 0.1% formic acid in water, and B was 0.1% formic acid in acetonitrile, at a flow rate of ~350 nL/min. Approximately 1/10 of each digest was injected at 5% B, then the organic content of the mobile phase was increased linearly to 50% over 30 min. The column effluent was directed to a QSTAR Pulsar tandem mass spectrometer (Applied Biosystems/MDS Sciex, Toronto, Calif.). During the elution of the peptides 1 sec MS acquisitions were followed by 5 sec CID experiments for computer-selected precursor ions in information-dependent acquisition mode. The collision energy was set according to the mass value and charge state of the precursor ion. The CID spectra were interpreted manually.

Protein class and function assessment was carried out with the aid of a variety of bioinformatics including database homology search engines [16] such as MS-Pattern and MS-BLAST.

We conducted 2D-gel analyses of neuronal axoplasm from the freshwater snail *Lymnaea stagnalis*; proteins differentially expressed in nerve regeneration were subjected to in-gel tryptic digestion followed by reverse phase chromatographic separation and mass spectral analysis of the digest mixture. Peptide sequences were deduced by interpretation of their collision-induced dissociation (CID) mass spectra, and used to query the NCBI nonredundant protein database to assign tentative homologies in sequenced genomes. This effort revealed a number of protein spots with extensive homology to intermediate filament proteins from other mollusks, including Helix [18] and Aplysia [19].

During the course of carrying out de novo sequencing of these particular proteins, a number of digest components were discovered during an LC-ESIMS experiment that displayed identical mass values for their entire CID sequence ion series (viz. identical fragmentation patterns), but eluted with significantly different chromatographic retention times (delta$T_R$=1–5 min) and possessed different molecular weights. In fact, all of the later eluting components of these identical fragmentation pattern pairs displayed an 80 Da increment in their measured molecular weight. Analysis of these LC-CIDMS spectra revealed eight such tryptic peptides in one particular digest. The chromatographic ion extraction profiles corresponding to the mass values of the modified peptides and their unmodified counterparts were retrieved from the entire digest LC/MS data set.

These data indicate analogs having identical peptide sequences modified by a moiety of $\Delta M$=80 Da. From the nominal mass spectrum, these modified analogs are stable during electrospray ionization under ambient conditions. This behavior indicated the modification was a sulfo-moiety, rather than the isobaric phospho-modification, consistent with results from protein phosphorylation studies [20–27].

Therefore, in order to establish that the observed modifications were due to O-sulfonation, a series of sulfo- and corresponding phospho-peptides was synthesized. For example, to compare the chromatographic retention and mass spectral fragmentation behavior, the sequence LAGLQDEIGSLR (SEQ ID NO:06) was synthesized as such together with its phospho- and sulfoseryl-analogs. These synthetic peptides were studied by LC/MS/MS under similar conditions to those employed during analyses of the original gel plug digests. The retention time observed for the sulfo-modified peptide was later than its unmodified counterpart noted in the original experiment vida supra. Interpretation of the results from these experiments including CID spectra established that the sulfo-peptides do eliminate the modification upon deposition of sufficient vibronic energy to induce dissociation of the peptide backbone bonds. They produce low energy CID mass spectra virtually identical to the corresponding unmodified molecules, but the phospho-serine analog undergoes only partial b-elimination [20–26]. Finally, we have observed that sulfo-threonyl peptides behave similarly to their sulfo-seryl analog molecules.

*Plasmodium falciparum* and human cell culture: In addition to the freshwater snail, similar experiments on digests derived from proteins isolated from both the malaria parasite, *Plasmodium falciparum*, and from human embryonic kidney 293T cells revealed peptide analogs that are covalently modified on both serine and threonine residues.

In the case of *Plasmodium falciparum*, one of the proteins was detected using a suicidal substrate probe for cysteine protease activity [14]. It was identified as a remote homolog of cathepsin C based on de novo sequences obtained from tandem mass spectrometry. One of its tryptic peptides has been shown by analogous CID analysis to be 7-O-sulfono-RIEVALTK (SEQ ID NO:09). This finding was confirmed by synthesis of this peptide and its modified analogs and subsequent measurements that showed comparable mass spectral behavior.

In addition, during mass spectrometric characterization of the myristyl juxtamembrane construct of the human tyrosine kinase receptor Ror2, the peptide $^{465}$LKEISLSAVR$^{474}$ (SEQ ID NO:10) was observed together with two other chromatographically distinct peaks. CID analyses of each of these produced fragmentation spectra demonstrative of sulfonation. These results indicate that this sequence exists modified at either of the two serine residues available for sulfonation.

The fragmentation behavior of phospho-peptides has been studied extensively for over a decade. It is well known that β-elimination of the elements of phosphoric acid (−98 Da) from Ser- and Thr-modified peptides occurs as a favored dissociation process [20–26]. However, quantitative elimination of phospho-functions does not occur either during electrospray ionization or under low energy collisional activation. Thus far the only observation of significant gas-phase dephosphorylation (−80 Da) during electrospray ionization involved the highly reactive phospho-histidine species [28]. Therefore the observations described above are diagnostic for the presence of a sulfo moiety, rather than the corresponding phospho-analog. Extensive previous studies have shown that Tyr-sulfated peptides usually display some sulfate loss even during MS acquisition [29].

Our identification of serine/threonine sulfonations in proteins from very different organisms demonstrates that this modification is widespread, occurring ubiquitously in eukaryotes. Moreover, the exemplified modified proteins we report are targeted to three distinct cell compartments, cytoplasm, lysosome, and plasma membrane, demonstrating that serine/threonine sulfonation occurs both in the ER continuum and the cytoplasm. Our studies also revealed a large number of proteins to be differentially sulfonated across differing physiological conditions, including injured versus non-injured axoplasms (Table 1).

TABLE 1

Differentially serine and threonine sulfonated proteins, including intermediate filament proteins.

| 1 | upregulated | IEF 3–10 | MW~26 kDa, pI~4 |
|---|---|---|---|
| 2 | upregulated | IEF 4.5–5.5 | MW~26 kDa; pI − 5 |
| 3 | upregulated | IEF 4.5–5.5 | MW~40 kDa, pI~4.6 |
| 5 | upregulated | IEF 4.5–5.5 | MW~110 kDa, pI − 5.3 |
| 6 | upregulated | IEF 4.5–5.5 | MW~108 kDa, pI − 5.4 |
| 7 | downregulated | IEF 4.5–5.5 | MW~99 kDa, pI 5.2 |
| 8 | downregulated | IEF 4.5–5.5 | MW~99 kDa, pI 5.3 |
| 9 | upregulated | IEF 4–7 | MW~26 kDa, pI 4.5 |
| 13 | upregulated | IEF 4–7~5 | high MW, pI |
| 15 | upregulated | IEF 4–7 | high MW, pI > 5 |
| 120 | downregulated | IEF 4–7 | contains sulfopeptides with similanty to synaptotagmin. |

TABLE 2

Differentially serine and threonine sulfonated peptides identified from CID in proteins 5, 6, 7, 8 and 9

| 5A | KVIDELASSK [131–140] | (SEQ ID NO: 01) |
|---|---|---|
| 5B | NAAYAELATR [340–349] | (SEQ ID NO: 02) |
| 5C | YASQLNQLR [304–312] | (SEQ ID NO: 03) |
| 5D | TLVEQAIGTQSK [428–439] | (SEQ ID NO: 04) |
| 6A | SSISPGVYQQLSSSGITDFK [47–66] | (SEQ ID NO: 05) |
| 6B | KVIDELASSK [131–140] | (SEQ ID NO: 01) |
| 6C | LAGLQDEIGSLR [147–158] | (SEQ ID NO: 06) |
| 6D | NAAYAELATR [340–349] | (SEQ ID NO: 02) |
| 6E | YASQLNQLR [304–312] | (SEQ ID NO: 03) |
| 6F | TLVEQAIGTQSK [428–439] | (SEQ ID NO: 04) |
| 7A | KVIDELASSK [131–140] | (SEQ ID NO: 01) |
| 7B | NAAYAELATR [340–349] | (SEQ ID NO: 02) |
| 8A | KVIDELASSK [131–140] | (SEQ ID NO: 01) |
| 8B | LAGLQDEIGSLR [147–158] | (SEQ ID NO: 06) |
| 8C | NAAYAELATR [340–349] | (SEQ ID NO: 02) |
| 8D | YASQLNQLR [304–312] | (SEQ ID NO: 03) |
| 8E | VGLRTLVEQAIGTQSK [424–439] | (SEQ ID NO: 07) |
| 8F | TLVEQAIGTQSK [428–439] | (SEQ ID NO: 04) |
| 9A | SSISPGVYQQLSSSGITDFK [47–66] | (SEQ ID NO: 05) |
| 9B | KVIDELASSK [131–140] | (SEQ ID NO: 01) |
| 9C | LAGLQDEIGSLR [147–158] | (SEQ ID NO: 06) |
| 9D | ELIVTYESQAK [159–169] | (SEQ ID NO: 08) |
| 9E | NAAYAELATR [340–349] | (SEQ ID NO: 02) |
| 9F | YASQLNQLR [304–312] | (SEQ ID NO: 03) |
| 9G | VGLRTLVEQAIGTQSK [424–439] | (SEQ ID NO: 07) |
| 9H | TLVEQAIGTQSK [428–439] | (SEQ ID NO: 04) |

II. Preparation of High-Affinity Single Chain Sulfopeptide Specific Anitibodies.

Nonimmune phage antibody libraries were constructed for the production of high-affinity human single-chain antibodies (Sheets et al., 1998, PNAS USA 95, 6157–62). Total RNA was prepared from three different samples of human spleen cells and from two different samples of human peripheral blood lymphocytes. cDNA was synthesized from total RNA primed with the HuIgMFOR primer (Marks, et al, 1991, J. Mol. Biol. 222, 581–597). $V_H$ gene repertoires were amplified from the cDNA by using Vent DNA polymerase (New England Biolabs) in combination with the HuIgM-FOR primer and an equimolar mixture of HuVHBACK primers. PCR products were agarose gel-purified and reamplified to append NcoI and NotI restriction sites by using Tth DNA polymerase (Epicentre Technologies, Madison, Wis.) and an equimolar mixture of the HuVHBACKSfi primers (that contain an NcoI site for cloning) and the HuCMForNot primer. The PCR products were cut with restriction enzymes NcoI and NotI and agarose gel-purified. The resulting DNA fragments were ligated into the plasmid pCITE3A (Novagen) cut with restriction enzymes NcoI and NotI and the ligated DNA was electroporated into the E. coli strain TG1. A library of $V_H$ genes containing $2.3 \times 10^8$ members was generated from the products of seven ligation reactions and 15 electroporations. The resulting library was termed pCITE-$V_H$. Cloning efficiency and library diversity was determined by PCR screening. The pCITE3A plasmid was used to create the $V_H$ gene repertoire because of the presence of unique sequences for PCR amplification that surround the NcoI and NotI cloning sites. These sequences allow the specific amplification of the $V_H$ genes for scFv assembly.

Construction of the scFv Library. The $V_H$ gene repertoire was PCR-amplified from the pCITE-$V_H$ library by using 300 ng of library plasmid DNA as a template, Vent DNA polymerase, the CITE3 primer, and an equimolar mixture of HuJ$_H$ primers. The $V_L$ genes for scFv assembly were obtained from a previously constructed scFv phage antibody library (Marks et al., supra). The $V_L$ gene repertoire, including DNA encoding the scFv peptide linker $(G_4S)_3$ (Huston, et al., 1988, PNAS USA 85, 5879–5883), was amplified from 300 ng of library plasmid DNA by using Vent DNA polymerase, the Gene3 primer, and an equimolar mixture of RHuJ$_H$ primers. The amplified $V_H$ and $V_L$ genes were agarose gel-purified and spliced together with overlap extension PCR to create a scFv gene repertoire (Clackson, et al., 1991, Nature, London, 352, 624–628). To accurately join $V_H$ and $V_L$ gene repertoires with overlap extension PCR, the input DNA fragments must have blunt ends. Therefore, the proofreading DNA polymerase Vent was used to generate the $V_H$ and $V_L$ DNA fragments for scFv assembly. For all subsequent PCR steps of library construction Tth DNA polymerase was found to be the optimal enzyme. The $V_H$ and $V_L$ gene repertoires were spliced together in 100-µl PCRs containing 100 ng of the $V_H$ and $V_L$ DNA fragments and Tth DNA polymerase. The reactions were cycled eight times (95° C. 2 min, 55° C., 1 min, and 72° C. 3 min) to join the fragments. Then the CITE3 and Gene3 primers were added and the reaction was cycled 30 times (94° C. 1 min, 55° C. 1 min, and 72° C. 3 min) to amplify the assembled scFv genes. The scFv genes were cut with restriction enzymes NcoI and NotI, agarose gel-purified, and ligated into the plasmid pHEN-1 (Hoogenboom, et al., 1991, Nucleic Acids Res. 19, 4133–4137) cut with NcoI and NotI. The ligated DNA was electroporated into E. coli TG1 cells.

Selection of Phage Antibodies. Phagemid particles were rescued from the library, as described (Schier, et al., 1996, J. Mol. Biol. 255, 28–43) except that the procedure was scaled up to 2 liters of culture media. Specific phage-displayed scFv were affinity-selected by using proteins absorbed to Immunotubes (Nunc). For selection of scFv to the sulfopeptides of Table 3, Immunotube selection is alternated with selection using decreasing concentrations of biotinylated sulfopeptides and capture of bound phage using streptavidin paramagnetic beads. Phage eluted from each selection are used to infect E. coli TG1 cells. Phage particles are rescued from the cells and used for the subsequent round of antigen selection. The rescue-selection-plating cycle is repeated 3–4 times, after which individual clones are analyzed for specific antigen binding by ELISA.

Antibody Binding Specificity. Binding specificity of all scFv is confirmed by ELISA using the target corresponding antigen sulfopeptide as substrate. Highly specific binding is indicated by "+++" or greater.

TABLE 3

High affinity single chain sulfopeptide specific antibodies

| Phage antibody | Sulfopeptide | SEQ ID NO | scFV specific binding |
|---|---|---|---|
| sT853 | 8-O-sulfono-KVIDELASSK | (SEQ ID NO: 01) | ++++ |
| sV107 | 9-O-sulfono-NAAYAELATR | (SEQ ID NO: 02) | ++++ |
| sR437 | 3-O-sulfono-YASQLNQLR | (SEQ ID NO: 03) | +++ |
| sR032 | 9-O-sulfono-TLVEQAIGTQSK | (SEQ ID NO: 04) | +++++ |
| sE209 | 14-O-sulfono-SSISPGVYQQLSSSGITDFK | (SEQ ID NO: 05) | +++ |
| sG576 | 10-O-sulfono-LAGLQDEIGSLR | (SEQ ID NO: 06) | ++++ |
| sB749 | 13-O-sulfono-VGLRTLVEQAIGTQSK | (SEQ ID NO: 07) | +++ |
| sY512 | 8-O-sulfono-ELIVTYESQAK | (SEQ ID NO: 08) | ++++ |
| sY268 | 7-O-sulfono-RIEVALTK | (SEQ ID NO: 09) | +++ |
| sU925 | 7-O-sulfono-LKEISLSAVR | (SEQ ID NO: 10) | ++++ |

III. Preparation of High-Affinity Sulfopeptide Specific Monoclonal Anitibodies.

A library of peptide conjugates was made by coupling the panel of O-linked serine- and threonine-sulfonated peptides of Table 3 with keyhole limpet hemocyanine (KLH). Our coupling protocol is essentially as described by Nishizawa et al. (1991, J Biol Chem 266, 3074–3079). Corresponding monoclonal antibodies are prepared essentially as described previously (Yano, et al. (1994) Biochem. Biophys. Res. Commun. 175, 1144–1151). In brief, KLH emulsified in complete Freund's adjuvant are injected intraperitoneally into BALB/c mice. A booster of the KLH-conjugate emulsion is given to the mice at 2-week intervals. Three days after the final boost, the spleen cells are fused with mouse myeloma cell SP2/0-Ag 14, using polyethylene glycol 4000. The hybridomas producing anti-sulfopeptide antibody were screened by enzyme-linked immunosorbent assay in microtiter plates coated with the sulfopeptides. The cells from positive wells are cloned twice to ensure monoclonality. In this manner, the hybridoma clone H32 producing AB32 antibody was developed. The hybridoma cells are grown as ascites tumors in BALB/c mice primed with pristane. Homogeneous IgG fractions are prepared by applying ascites fluid on protein A-gel (Bio-Rad) and eluting it, according to the manufacturer's instructions. Immediately after the elution, IgG proteins are dialyzed against PBS.

IV. Mutating Sulfonated Residues of Differentially Sulfonated Axoplasma Proteins.

Differentially sulfonated axoplasma proteins 5, 6, and 8 (DSAP5, DSAP6 and DSAP8, respectively) are sulfonated on serine/threonine residues 138, 51 and 436, respectively (Ser-138, Ser-51 and Thr-436, respectively). This example describes cell lines expressing these proteins with sulfonated serine/threonine residues converted to either Glu or Phe, and subsequent in situ immunolocalization of the mutant proteins under different axon conditions. These experiments reveal that the targeted sulfonation influences cellular localization of DSAP5, DSAP6 and DSAP8. Experimental protocols were adapted from Dong et al., Biochemistry, 1994; 33(46); 13946–53.

Polymerase chain reaction-based site-directed mutagenesis is performed using a commercial kit (QuickChange™, Stratagene, La Jolla, Calif.) directly on the mammalian expression vector pDX containing DSAP cDNA. By this method, codons for the subject Ser-138, Ser-51 and Thr-436 are converted to codons for either phenylalanine or glutamic acid. The mutant constructs are sequenced in their entirety to verify targeted mutations. The sequencing reaction is performed using a dye terminator kit, and the results analyzed on an ABI model 737A automated sequencer (ABI, San Leandro, Calif.).

The mutant and wild-type DSAP constructs are cotransfected into PC12 cells, which differentiate in the presence of NGF to a neuron-like phenotype. The plasmid pcDNA3 is transfected by electroporation; cotransfection with the DSAP mutants allows for selection of mutant-expressing cells by growth under G418 or geneticin; see, e.g. Tcherpakov et al, 2002-J. Biol Chem 277: 49101–49104. Transfected cells are first grown in alpha-minimal essential medium (a-MEM, Life Technologies, Inc.) without fetal bovine serum for 12–18 h and then grown in complete a-MEM medium supplemented with 10% heat-inactivated fetal bovine serum (Life Technologies, Inc.). For transient expression, cells are harvested 72 h after transfection. To establish stable cell lines, transfected cells are grown in complete a-MEM containing 500 µg/ml hygromycin (Calbiochem). The cells are assayed for DSAP expression and localization by staining fixed, membrane-solublized cells in 1 µg/ml monoclonal antibody (supra) and immunostaining with sheep anti-mouse IgG-fluorecein.

V. Sulfospecific Proteolysis: Chemoenzymatic Mapping Sites of Protein Sulfonation.

This example employs the selective chemical transformation of sulfoserine and sulfothreonine residues into lysine isosteres (aminoethylcysteine and β-methylaminoethylcysteine, respectively). Aminoethylcysteine-modified peptides are then selectively cleaved with a lysine-specific protease to map sites of sulfonation. A blocking step enables single-site cleavage when desired, and adaptation of this reaction to the solid phase facilitates sulfopeptide enrichment and modification in one step. Our strategy relies on the well-established β-elimination of sulfoserine residues to generate dehydroalanine under basic conditions (sulfothreonine is converted to β-methyldehydroalanine). Similar chemistry has been used to enrich and quantitate phosphoproteins for traditional trypsin digestion and MS/MS sequencing. In the next step, dehydroalanine acts as a Michael acceptor for cysteamine, generating an aminoethylcysteine residue (for sulfothreonine, β-methylaminoethylcysteine is generated). Since aminoethylcysteine is isosteric with lysine, proteases that recognize lysine (e.g. trypsin, Lys-C, and lysyl endopeptidase) will cleave proteins at this residue. We adapted this strategy from an analogous approach for mapping protein phosphorylation (Knight et al., Nat Biotechnol. 2003 Aug. 17, Epub ahead of print).

A panel of sulfoserine and two sulfothreonine peptides was chosen to demonstrate the feasibility of this approach. Extensive peptide degradation results when standard β-elimination conditions (~1M hydroxide, 42–55° C., >1 hour) are applied. To achieve quantitative β-elimination without peptide hydrolysis, we use barium hydroxide as the base, as well as a specific catalyst for sulfate elimination, at a concentration of 50 mM; carry out reactions in a previously optimized mixture of DMSO, water, and ethanol; limit the reaction length and temperature; and perform the β-elimination and Michael addition steps consecutively, such that the addition of cysteamine to the basic reaction mixture in the second step reduces the pH of the reaction to ~8. Using this procedure, each peptide is cleanly converted into its aminoethylcysteine or β-methylaminoethylcysteine analogue. Digestion of the aminoethylcysteine modified peptides with Lys-C or trypsin liberates peptide fragments corresponding to selective cleavage at the site of serine sulfonation. Hence, site-specific modification combined with proteolytic digestion allows for the unambiguous identification of serine and threonine sulfonation sites from the exact masses of the liberated fragments.

We also selected a model protein (the human tyrosine kinase receptor Ror2) that contains multiple sites of O-sulfonation to demonstrate this strategy for mapping sulfonation sites. Here, the protein is subject to aminoethylcysteine modification followed by co-digestion with trypsin or Lys-C. One pmol digested protein is separated by nanoflow liquid chromatography on a nano-C18 column and then directly analyzed by online LC-MS, and MS/MS on a quadrupole orthogonal TOF spectrometer (QSTAR instrument, PESciex). Peptides are identified by mass fingerprinting (ESI-MS) corresponding to direct cleavage at all predicted sulfonation sites of the proteins, as well as by CID data.

In some cases, it is desirable to obtain cleavage exclusively at the sulfonation site (not at lysine residues), generating larger fragments that might provide information about the gross topology of sulfonation. For example, the coexistence of unique sulfoisoforms (variants of a single protein that contain distinct combinations of sulfonated residues) could be investigated by this type of digestion. The structure of such sulfoisoforms is challenging to probe by traditional methods, since trypsin digestion intrinsically disconnects information about sulfonation sites that are separated by more than 10 to 20 residues (the frequency of a lysine or arginine residue). Alternatively, cleavage exclusively at sulfonation sites facilitates sulfonation mapping by N-terminal Edman degradation, since the first residues sequenced are those directly C-terminal to the site of sulfonation.

The MARCKS substrate, a 25 residue peptide containing 12 lysine and modified to contain three sulfoserine residues, was selected to explore the feasibility of achieving exclusive cleavage at sulfonation sites. To do this, we first convert the lysine residues to homoarginine using o-methylisourea in order to block digestion at those sites with Lys-C. In addition to blocking proteolytic digestion, this modification has several practical advantages, including (I) the enhancement of the ionization of homoarginine containing peptides in MALDI due to the introduction of the more basic guanidinium moiety, (ii) the elimination of the near mass degeneracy of lysine and glutamine, simplifying database searching based on mass fingerprinting, (iii) the retention of the positive charge of the lysine modified peptides and proteins, improving solubility, and (iv) reaction conditions that can facilitate the nearly quantitative (90–99%) guanidination of the lysine residues in full-length proteins.

The MARCKS substrate is guanidinated, the sulfoserine residues further converted to aminoethylcysteine, digested with Lys-C, and finally subjected to mass analysis by MALDI. The MALDI mass spectrum from the digest exhibits eight prominent peaks corresponding to eight of nine possible combinations of cleavage at the three sulfonation sites. The smallest fragment, corresponding to cleavage at aminoethylcysteine residues 8 and 12 (m/z=652.4), requires longer digestion times and higher concentrations of protease to detect. No other major products are observed, confirming that homoarginine is not a substrate for Lys-C. Alternative chemistries are available for efficiently blocking lysine residues, and similar results are obtained with the MARCKS substrate by acetylating the lysines residues.

We also sought to couple aminoethylcysteine modification directly to an approach for sulfopeptide enrichment. For this purpose, we adapt the aminoethylcysteine reaction to a solid phase catch and release strategy to provide one step modification and enrichment of sulfopeptides. This strategy allows sulfopeptides to be captured in the first step through an irreversible reaction with the dehydroalanine moiety. In the next step, a different bond in the bead linker is labilized such that peptides are released while simultaneously unmasking a new chemical handle (aminoethylcysteine) for subsequent enzymatic interrogation. This type of approach facilitates automation and offers advantages over similar enrichment approaches that rely on selective biotinylation, which has been observed to complicate MS spectra.

To prepare an appropriate solid phase reagent, a polyethyleneglycol-polystyrene (PEG-PS) copolymer base resin (TentaGel AC) is loaded with cystamine as the benzyl carbamate. This design incorporates two important features that facilitate aminoethylcysteine modification. First, the PEG-PS resin swells in both organic and aqueous solvents, allowing resin capture to be performed under conditions that have been optimized and validated for the solution phase chemistry. Secondly, the methoxybenzyl carbamate linkage is stable to the basic conditions of the β-elimination reaction, allowing for efficient peptide capture, but highly acid labile, facilitating aminoethylcysteine peptide release by brief treatment with trifluoroacetic acid (TFA).

We test the ability of this reagent to capture sulfopeptides and release them as the aminoethylcysteine derivative. Two non-sulfonated peptides, one sulfonated threonine peptide, and one sulfoserine peptide are mixed and added to the resin as an approximately equimolar mixture. After incubation with the resin under β-elimination conditions for one hour, the flow-through is analyzed by HPLC. The non-sulfonated peptides are detected intact, but the sulfoserine and sulfothreonine peaks are absent, consistent with selective capture of the sulfopeptides in high yield. Brief treatment with TFA releases the sulfopeptides as the aminoethylcysteine modified diastereomer pair, suitable for enzymatic sulfonation mapping. This approach allows proteolytic sulfonation site-mapping to be directly coupled to sulfopeptide enrichment from complex mixtures.

In summary, we describe here an approach for mapping protein sulfonation by direct enzymatic cleavage of polypeptides at the site of post-translational modification. This strategy is also applicable to mapping protein phosphorylation and glycosylation in an analogous fashion. Methods for distinguishing between these various O-modifications are well-established, such as pretreatment with an appropriate glycosidase or phosphatase.

Details of the experimental protocols used in this example are as follows:

Sulfonation Mapping of Sulfoserine and Sulfothreonine Peptides. Model sulfoserine peptides (ca. 100 μg) are dissolved in a 4:3:1 solution of $H_2O:DMSO:EtOH$ (50 μL). The β-elimination solution (50 mM $Ba(OH)_2$ solution (23 μl) is added, and the reaction is incubated at 37° C. After 1 hour, a 1M solution of cysteamine in $H_2O$ (50 μl) is added directly to this reaction and the reaction incubated an additional hour at room temperature. Reactions are analyzed by dilution into 1 ml $H_2O$/0.1% TFA and separation of the reaction products by reverse phase HPLC on a Dynamax SD-200 solvent delivery system (Rainin, Woburn, Mass.) equipped with a C-18 column. Individual fractions are analyzed by ESI-MS offline using a Micromass ZQ (Waters, Milford, Mass.) or by MALDI-MS and ESI-MS/MS. (below). Beta-elimination was also performed as follows: to 2 ul peptide solutions (1 pM/ul in water) we added 2 ul of 25 mM $Ba(OH)_2$, incubated for 1 hr at 37° C., added 2 ul of 25 mM ammonium sulfate, centrifuged it, took 1 ul of the supernatant, and measured it by MALDI in DHB without further purification.

For site-mapping, modified peptides are reconstituted in either 10 mM Tris, pH 8.5 (Trypsin) or 10 mM Tris, pH 8.5, 1 mM EDTA (Lys-C) and digested for 4 hrs at 37° C. Reactions are analyzed as above. For FRET monitoring of the Lys-C digestion of diastereomeric aminoethylcysteine peptides, peptide diastereomers (~5 μg) are separated by HPLC, and digested with 5 μg Trypsin. Reaction progress is monitored as emission at 420 nm following excitation at 320 nm in a SpectraMax GeminiXS fluorescence plate reader (Molecular Devices, Sunnyvale, Calif.) as described.

For guanidination reactions, the MARCKS substrate or β-casein was dissolved in 0.5 M O-methylisourea, pH 10.5 and incubated overnight at 37° C. For acetylation reactions, the MARCKS substrate was dissolved in 100 mM $NaHCO_3$, pH 8.5 and treated with approximately 100 equivalents of sulphosuccinimidyl acetate (Pierce, Rockford, Ill.) for 2 hours at room temperature to quantitatively acetylate lysine residues. Reactions were desalted by HPLC or dialysis and subjected to aminoethylcysteine modification and Lys-C digestion as above.

Mass spectra are obtained by matrix-assisted laser desorption ionization time-of-flight (MALDI-TOF) mass spectrometry on a Voyager DESTR (Applied Biosystems, Framingham, Mass.). All mass spectra are acquired in positive-ionization mode with reflectron optics. The instrument is equipped with a 337 nm nitrogen laser and operated under delayed extraction conditions in reflectron mode; a delay time of 200 nsec, and grid voltage 72.5% of full acceleration voltage (20 kV); the guide wire voltage is at 0.002%. For linear mode experiments, the delay time is 85 nsec and the grid voltage 94% of the acceleration voltage; the guide wire voltage is at 0.05%. Prior to MALDI-MS analysis, the proteolytic reaction mixtures are desalted with reversed-phase Zip Tips$_{C18}$ (C-18 resin, Millipore, Bedford, Mass.). All peptide samples are prepared using a α-cyano-4-hydroxycinnamic acid (HCCA) (Agilent Technologies) matrix solution or 2,5-dihydroxy benzoic acid, saturated solution in water; 1 μL of analyte (0.1–1 pmol of material) is mixed with 1 μL of matrix solution, and then air-dried at room temperature on a stainless steel target. Typically, 200 laser shots are used to record each spectrum. The obtained mass spectra are externally calibrated with an equimolar mixture of angiotensin I, ACTH 1–17, ACTH 18–39, and ACTH 7–38.

Sulfonation Mapping of Ror2. Human Ror2 protein (ca. 100 μg) is modified using the same conditions as described for peptides. Following aminoethylcysteine modification, the protein is transferred to the digestion buffer by gel filtration (PD-10, Amersham Biosciences, Piscataway, N.J.). Sequential digests with Trypsin or Lys-C are carried out at 37° C. for approximately 6 hours each using ca. 1/10 enzyme by weight.

For manipulation of smaller sample sizes (50 ng to 4 μg), several modifications were made to the above protocol. Aminoethylcysteine modification is carried out in 0.5 ml microcentrifuge tubes and the sample volume is adjusted to maintain a protein concentration greater than or equal to 0.01 μg/μl. When the reaction is complete, reagents are removed by dialysis overnight against 1 liter of 20 mM Tris, pH 8.0 using 10000 MWCO Slide-A-Lyzer Mini Dialysis units (Pierce, Rockford, Ill.). Dialyzed samples are transferred to a new 0.5 ml microcentrifuge tube, and the dialysis membrane is washed three times with 10 μl of 20 mM Tris, pH 8.0. Samples are concentrated to ~5 μl by Speedvac and 5 μl of acetonitrile added as a denaturant. The sample mixture is heated to 65° C. for 10 minutes and then the digestion is initiated by the addition of 15 μl of 10 mM Tris, pH 8.0 containing trypsin at 1/10 enzyme to substrate by weight. Reactions are allowed to proceed approximately 6 hours at 37° C.

The proteolytic peptide mixtures (ca. 1 pmol) are analyzed by MALDI-MS or by reversed-phase HPLC-MS/MS. Briefly, peptides are separated on an Ultimate nanocapillary HPLC system equipped with a PepMap™ C18 nano-column (75 μm I.D.×15 cm) (LC Packings, Sunnyvale, Calif.) and CapTrap Micro guard column (0.5 μl bed volume, Michrom, Auburn, Calif.). Peptide mixtures are loaded onto the guard column and washed with the loading solvent ($H_2O$/0.05% formic acid, flow rate: 20 μl/min) for 5 min to remove salts and denaturing reagents, then transferred onto the C18-nanocapillary HPLC column and eluted at a flow rate of 300 nl/min using the following gradient: 2% B (from 0–5 min), and 2–70% B (from 5–55 min). Solvent A consists of 0.05% formic acid in 98% $H_2O$/2% ACN and solvent B consists of 0.05% formic acid in 98% ACN/2% $H_2O$. The column eluant is directly coupled to QSTAR quadrupole orthogonal TOF mass spectrometer (MDS Sciex, Concorde, Canada) equipped with a MicroIonSpray source (MDS Sciex, Concorde, Canada). The needle voltage is typically 2300 V in the HPLC-MS mode. Mass spectra (ESI-MS) and tandem mass spectra (ESI-MS/MS) are recorded in positive-ion mode with a resolution of 10,000 FWHM. For collision induced dissociation tandem mass spectrometry (CID-MS/MS), the mass window for precursor ion selection of the quadrupole mass analyzer is set to ±3 mass unit. The precursor ions are fragmented in a collision cell using nitrogen as the collision gas. The LC-MS runs on the QSTAR instrument are acquired in "Information Dependent Acquisition" mode, which allows the user to acquire MS/MS spectra based on an inclusion/exclusion mass list/charge states and dysnamic assessment of relative ion intensities. The instrument is calibrated by infusing a renin peptide standard and using its MS/MS fragment-ions (His immonium-ion at m/z at 110.0713, and $b_8$-ion at m/z at 1028.5312) providing a mass accuracy of ≦50 ppm.

Resin Synthesis. Tentagel AC resin (5 g) is swelled in anhydrous THF (75 ml) at room temperature under an inert atmosphere. 1,1 carbonyldiimidazole (2.5 g) is added and stirred for 3 hours. The resin is filtered, washed with THF, $Et_2O$, and dried in vacuo overnight. Before use, cystamine HCl salt (5 g) is dissolved in $H_2O$ (45 ml), the pH is adjusted to 12 with NaOH, and the cystamine is extracted with $CH_2Cl_2$. The organic phase is dried with $MgSO_4$, filtered, and the solvent removed in vacuo to give a clear oil. This oil (ca. 1 g) is added to the activated resin (2 g) swelled in THF (25 ml). N-methylmorpholine (2 ml) is added and the resin is heated to 60° C. for 4–6 hours under an inert atmosphere. The resin is filtered, washed with THF, $Et_2O$, dried in vacuo, and stored at −20° C. Immediately before use, the resin is deprotected by brief treatment (15 min.) with 100 mM DTT in $H_2O$ to expose the cysteamine thiol. Quantitation of resin loading with Ellman's reagent typically demonstrates 60–80% loading (0.20 to 0.25 mmol/g).

Solid-Phase Capture and Modification of Sulfoserine Peptides. Following deprotection, the resin is washed with 5 times with $H_2O$ and 5 times with 4:3:1 $H_2O$:DMSO:EtOH. Peptides are dissolved in 4:3:1 $H_2O$:DMSO:EtOH (250 μl) and added to 80 mg of resin swollen in the same. 50 mM $Ba(OH)_2$ (225 μl) is added and the reaction is incubated for one hour at 37° C. The resin is then rinsed successively with $H_2O$, DMF, $CH_2Cl_2$ and $Et_2O$ and dried overnight in vacuo. To release the peptides, the dried resin is suspended in 95:2.5:2.5 TFA:$Me_2S$:$H_2O$ (1 ml) for 15 minutes at room temperature. The resin is then filtered, washed 3 times with TFA (1 ml), and the filtrate is concentrated in vacuo. The released peptides are taken up in $H_2O$/0.1% TFA and analyzed by HPLC (abs. 215 nm) and MS.

Supplementary Aminoethylcysteine Modification Protocol. Protein samples for aminoethylcysteine modification are first desalted overnight by microdialysis against 2 liters water using 10000 MWCO Slide-A-Lyzer Mini Dialysis units. Before use, dialysis units are soaked for one hour in water and the inner membrane is rinsed three times with 100 μl water. Following dialysis, dialyzed samples are transferred to 0.5 ml eppendorf tubes, and the dialysis membrane is washed three times with 20 μl water. The combined dialyate is then concentrated by Speed-Vac to reduce volume to ~5 μl, with care not to concentrate to dryness. 5 μl of a 3:1 mixture of DMSO:EtOH is added directly to this sample. β-elimination is initiated by the addition of 4.6 μl sat. $Ba(OH)_2$ and 1 μl NaOH. For most proteins, a 2 hour incubation in a 37° C. water bath is recommended. At this stage, solutions of some full-length proteins may appear somewhat heterogeneous; this has no effect on the efficiency of the reaction, but gentle vortexing every 20 or 30 minutes is recommended to prevent excessive aggregation. After two hours, the sample is placed at room temperature. While the sample is cooling (5–10 minutes), a 1 M solution of cysteamine HCl is freshly prepared, and 10 μl of this solution is added directly to the β-elimination reaction. This reaction is allowed to proceed 3 to 6 hours at room temperature.

When the Michael addition reaction is complete, the protein solution is transferred to a rinsed mini-dialysis unit and dialyzed overnight against 2 liters of 20 mM Tris, pH 8.0. The eppendorf tube from the b-elimination reaction is rinsed three times with 15 ml of 20 mM Tris, pH 8.0 to ensure complete protein transfer. Following dialysis, the protein is transferred to a new 0.5 ml eppendorf tube, with careful rinsing of the dialysis membrane. This protein solution is then concentrated by Speed-Vac. This concentrated protein sample is then ready for digestion with appropriate proteases (e.g., trypsin or Lys-C) and analysis by LC-MS/MS or MALDI-MS. In general, we find that Lys-C cleaves at modified sites more efficiently than trypsin, and that it is advisable to use slightly higher concentrations of proteases than would be optimal for an ordinary trypsin digestion, although optimal digestion conditions vary significantly between samples.

CITED REFERENCES

1. Strott, C. A. (2002) *Endocrine Revs.* 23, 703–732.
2. Robbins P., & Lippmann, F. (1956) *J. Am. Chem. Soc.* 78, 2652.
3. Huxtable, R. J. (1986) *Biochemistry of Sulfur*, (Plenum, NY).
4. Moore, K. L. (2003) *J. Biol. Chem.* May 2 Manusc. R300008200.
5. Kehoe J. W., & Bertozzi, C. R. (2000) *Chem. Biol.* 7, R57–R61.
6. Beisswanger, R. et al., (1998) *Proc. Natl. Acad. Sci. USA* 95, 11134–11139.
7. Kakuta, Y. et al., (1998) *Trends Biochem. Sci.* 129–130.
8. Parenti, G., Meroni, G. & Ballabio, A. (1997) *Curr. Opin. Genetics Dev.* 7, 386–391.
9. Cohen, P. (2002) *Nature Cell Biol.* 4, E127–E130.
10. Huttner, W. B. (1984) *Meth. Enzymol.* 107, 200–223.
11. Krishna R. & Wold, F. (1998) in *Proteins Analysis and Design*, ed. Angeletti, R. H. (Academic Press, San Diego, Calif.) pp 121–206
12. Medzihradszky K. F. & Burlingame, A. L. (1994) *Methods: A Companion to Methods in Enzymology* 6, 84–303.
14. Greenbaum, et al. (2000) *Chem. Biol.* 7, 569–581
16. Huang, et al. (2001) *J. Biol. Chem.* 276, 28327–28339.
18. Dodemont, H., Riemer, D., & Weber, K., (1990) *EMBO J.* 9, 4083–4094.
19. Sweatt, et al. (1989) *Electrophoresis* 10, 152–157.
20. Gibson, et al. (1987) *J. Am. Chem. Soc.* 109, 5343–5348.
21. Payne, et al. (1991) *EMBO J.* 10, 885–892.
22. Tsutakawa, et al. (1995) *J. Biol. Chem.* 270, 26807–26812.
23. Carr, S. A., Huddleston, M. J., & Annan, R. S. (1996) *Anal Biochem* 239, 180–192.
24. deCarvalho, et al. (1996) *J. Biol Chem* 271, 6987–6997.
25. Neville, et al. (1997) *Protein Sci* 6, 2436–2445.
26. Bean, et al. (1995) in *Techniques in Protein Chemistry* Vol. VI, ed. Crabb, J. W., (Academic, San Diego, Calif.), pp 107–116
28. Medzihradszky, et al. (1997) *Protein Science* 6, 1405–1411.
29. Wolfender, et al. (1999) *J. Mass Spectrom.* 34, 447–454.

The foregoing descriptions of particular embodiments and examples are offered by way of illustration and not by way of limitation. All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of detecting a post-translational modification of a predetermined protein expressed by a cell, comprising the step of: specifically detecting an O-sulfonation of a serine or threonine residue of the protein, wherein the O-sulfonation is detected using (a) a sulfopeptide-specific antibody, (b) chemical analysis to detect chemically labeled O-serine or O-threonine sulfonation, (c) radiolabeling with $^{35}SO_4$ to detect radiolabeled O-serine or O-threonine sulfonation, or (d) mass fragmentation analysis by mass spectrometry.

2. The method of claim 1, wherein the detected O-sulfonation is detected under a first physiological condition, and is compared with a control O-sulfonation detected under a second physiological condition.

3. The method of claim 1 wherein the O-sulfonation is detected using a sulfopeptide-specific antibody.

4. The method of claim 1 wherein the O-sulfonation is detected using chemical analysis to detect chemically labeled O-serine or O-threonine sulfonation.

5. The method of claim 1 wherein the O-sulfonation is detected using radiolabeling with $^{35}SO_4$ to detect radiolabeled O-serine or O-threonine sulfonation.

6. The method of claim 1 wherein the O-sulfonation is detected using mass fragmentation analysis by mass spectrometry.

* * * * *

UNITED STATES PATENT AND TRADEMARK OFFICE
CERTIFICATE OF CORRECTION

PATENT NO.         : 7,138,228 B2
APPLICATION NO. : 10/657027
DATED              : November 21, 2006
INVENTOR(S)        : Burlingame et al.

Page 1 of 1

It is certified that error appears in the above-identified patent and that said Letters Patent is hereby corrected as shown below:

On Title page Item (73), address of second assignee (Yeda Research and Development Co. Ltd. at the Weizmann Institute of Science) should read: "Rehovot, Israel", not Oakland, CA.

Signed and Sealed this

Twenty-fifth Day of November, 2008

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 10
<212> TYPE: PRT
<213> ORGANISM: Lymnaea stagnalis

<400> SEQUENCE: 1

Lys Val Ile Asp Glu Leu Ala Ser Ser Lys
1               5                   10

<210> SEQ ID NO 2
<211> LENGTH: 10
<212> TYPE: PRT
<213> ORGANISM: Lymnaea stagnalis

<400> SEQUENCE: 2

Asn Ala Ala Tyr Ala Glu Leu Ala Thr Arg
1               5                   10

<210> SEQ ID NO 3
<211> LENGTH: 9
```

```
<212> TYPE: PRT
<213> ORGANISM: Lymnaea stagnalis

<400> SEQUENCE: 3

Tyr Ala Ser Gln Leu Asn Gln Leu Arg
1               5

<210> SEQ ID NO 4
<211> LENGTH: 12
<212> TYPE: PRT
<213> ORGANISM: Lymnaea stagnalis

<400> SEQUENCE: 4

Thr Leu Val Glu Gln Ala Ile Gly Thr Gln Ser Lys
1               5                   10

<210> SEQ ID NO 5
<211> LENGTH: 20
<212> TYPE: PRT
<213> ORGANISM: Lymnaea stagnalis

<400> SEQUENCE: 5

Ser Ser Ile Ser Pro Gly Val Tyr Gln Gln Leu Ser Ser Ser Gly Ile
1               5                   10                  15

Thr Asp Phe Lys
            20

<210> SEQ ID NO 6
<211> LENGTH: 12
<212> TYPE: PRT
<213> ORGANISM: Lymnaea stagnalis

<400> SEQUENCE: 6

Leu Ala Gly Leu Gln Asp Glu Ile Gly Ser Leu Arg
1               5                   10

<210> SEQ ID NO 7
<211> LENGTH: 16
<212> TYPE: PRT
<213> ORGANISM: Lymnaea stagnalis

<400> SEQUENCE: 7

Val Gly Leu Arg Thr Leu Val Glu Gln Ala Ile Gly Thr Gln Ser Lys
1               5                   10                  15

<210> SEQ ID NO 8
<211> LENGTH: 11
<212> TYPE: PRT
<213> ORGANISM: Lymnaea stagnalis

<400> SEQUENCE: 8

Glu Leu Ile Val Thr Tyr Glu Ser Gln Ala Lys
1               5                   10

<210> SEQ ID NO 9
<211> LENGTH: 8
<212> TYPE: PRT
<213> ORGANISM: Lymnaea stagnalis

<400> SEQUENCE: 9

Arg Ile Glu Val Ala Leu Thr Lys
1               5

<210> SEQ ID NO 10
```

```
-continued

<211> LENGTH: 10
<212> TYPE: PRT
<213> ORGANISM: Lymnaea stagnalis

<400> SEQUENCE: 10

Leu Lys Glu Ile Ser Leu Ser Ala Val Arg
1               5                   10
```